(12) United States Patent
Kojima

(10) Patent No.: US 11,896,410 B2
(45) Date of Patent: Feb. 13, 2024

(54) PHOTON COUNTING CT APPARATUS AND METHOD OF CORRECTING MATERIAL DECOMPOSITION MAP

(71) Applicant: FUJIFILM Healthcare Corporation, Chiba (JP)

(72) Inventor: Shinichi Kojima, Chiba (JP)

(73) Assignee: FUJIFILM Healthcare Corporation, Chiba (JP)

( * ) Notice: Subject to any disclaimer, the term of this patent is extended or adjusted under 35 U.S.C. 154(b) by 225 days.

(21) Appl. No.: 17/457,315

(22) Filed: Dec. 2, 2021

(65) Prior Publication Data

US 2022/0211338 A1  Jul. 7, 2022

(30) Foreign Application Priority Data

Jan. 6, 2021 (JP) ................................. 2021-001124

(51) Int. Cl.
*A61B 6/00* (2006.01)
*A61B 6/03* (2006.01)

(52) U.S. Cl.
CPC ............ *A61B 6/4241* (2013.01); *A61B 6/032* (2013.01); *A61B 6/4035* (2013.01)

(58) Field of Classification Search
CPC ..... A61B 6/4241; A61B 6/032; A61B 6/4035; A61B 6/5217; A61B 6/58; A61B 6/583; A61B 6/035; A61B 6/46; A61B 6/582; A61B 6/585; G01N 23/046; G01N 23/223
See application file for complete search history.

(56) References Cited

U.S. PATENT DOCUMENTS

2021/0106292 A1*  4/2021  Kojima ................. A61B 6/582

FOREIGN PATENT DOCUMENTS

| JP | 2016-193174 | 11/2016 |
| JP | 2019-037550 A | 3/2019 |
| JP | 2019-176988 | 10/2019 |
| JP | 2019-532699 A | 11/2019 |
| WO | WO2014/163187 A1 | 10/2014 |

OTHER PUBLICATIONS

Japanese official action dated Aug. 22, 2023 (and English translation thereof) in connection with corresponding Japanese Patent Application No. 2021-001124.

* cited by examiner

*Primary Examiner* — Courtney D Thomas
(74) *Attorney, Agent, or Firm* — Paul Teng

(57) ABSTRACT

A photon counting computed tomography (CT) apparatus actually measures corrective measurement values by radiating X-rays from an X-ray tube and counting X-ray photons in each of a plurality of energy bands in a vacant state in which no subject is arranged in an imaging range of the photon counting CT apparatus and/or in a state in which one or more types of corrective materials are arranged at a position through which X-rays radiated from the X-ray tube pass, and corrects measurement values in a material decomposition map based on the actually measured corrective measurement values.

12 Claims, 12 Drawing Sheets

FIG. 2

COUNTING VALUES

|  | Ch1 | Ch2 | ... | Ch n-1 | Ch n |
|---|---|---|---|---|---|
| ENERGY BAND 1 (bin 1) | 1010 | ... |  |  |  |
| ENERGY BAND 2 (bin 2) | 1521 | ... |  |  |  |
| ENERGY BAND 3 (bin 3) | 1270 | ... |  |  |  |

| | | | FAT | | | | |
|---|---|---|---|---|---|---|---|
| | | | 0mm | 50mm | 100mm | 150mm | 200mm |
| BONE | 0mm | bin1 | 2000 | 1748 | 1529 | 1337 | 1169 |
| | | bin2 | 3000 | 2706 | 2441 | 2202 | 1987 |
| | | bin3 | 2500 | 2280 | 2080 | 1897 | 1731 |
| | 2mm | bin1 | 1916 | 1675 | 1465 | 1281 | 1120 |
| | | bin2 | 2954 | 2665 | 2404 | 2169 | 1957 |
| | | bin3 | 2478 | 2261 | 2062 | 1881 | 1716 |
| | 4mm | bin1 | 1835 | 1605 | 1403 | 1227 | 1073 |
| | | bin2 | 2909 | 2624 | 2367 | 2136 | 1927 |
| | | bin3 | 2457 | 2241 | 2045 | 1865 | 1701 |
| | 6mm | bin1 | 1758 | 1538 | 1344 | 1176 | 1028 |
| | | bin2 | 2864 | 2584 | 2331 | 2103 | 1897 |
| | | bin3 | 2436 | 2222 | 2027 | 1849 | 1687 |
| | 8mm | bin1 | 1685 | 1473 | 1288 | 1126 | 985 |
| | | bin2 | 2820 | 2544 | 2295 | 2071 | 1868 |
| | | bin3 | 2415 | 2203 | 2010 | 1834 | 1673 |

FIG. 5A

CURRENT CORRECTIVE MATERIAL MAP (CORRECTIVE MEASUREMENT VALUES) 411

| | | ACRYLIC | | | |
|---|---|---|---|---|---|
| | ENERGY | 0 mm | 50 mm | 100 mm | ... |
| ALUMINUM | 0 mm | | | | |
| | bin1 | 2000 | 1748 | 1529 | |
| | bin2 | 3000 | 2706 | 2441 | |
| | bin3 | 2500 | 2280 | 2080 | |
| | 5 mm | | | | |
| | bin1 | 1916 | 1675 | 1465 | |
| | bin2 | 2954 | 2665 | 2404 | |
| | bin3 | 2478 | 2261 | 2062 | |
| | 10 mm | | | | |
| | bin1 | 1835 | 1605 | 1403 | |
| | bin2 | 2909 | 2624 | 2367 | |
| | bin3 | 2457 | 2241 | 2045 | |
| | : | : | | | |

FIG. 5B

PRESENT-MOMENT CORRECTIVE MATERIAL MAP (CORRECTIVE MEASUREMENT VALUES) 412

| | | ACRYLIC | | | |
|---|---|---|---|---|---|
| | ENERGY | 0 mm | 50 mm | 100 mm | ... |
| ALUMINUM | 0 mm | | | | |
| | bin1 | 2050 | | 1553 | |
| | bin2 | 3100 | | 2499 | |
| | bin3 | 2525 | | 2100 | |
| | 5 mm | | | | |
| | bin1 | | | | |
| | bin2 | | | | |
| | bin3 | | | | |
| | 10 mm | | | | |
| | bin1 | 1840 | | | |
| | bin2 | 2910 | | | |
| | bin3 | 2470 | | | |
| | : | : | | | |

 

412-1

| | | ACRYLIC | | | |
|---|---|---|---|---|---|
| | ENERGY | 0 mm | 50 mm | 100 mm | ... |
| ALUMINUM | 0 mm | | | | |
| | bin1 | 2050 | 1784 | 1553 | |
| | bin2 | 3100 | 2783 | 2499 | |
| | bin3 | 2525 | 2302 | 2100 | |
| | 5 mm | | | | |
| | bin1 | 1943 | 1690 | 1472 | |
| | bin2 | 3004 | 2697 | 2421 | |
| | bin3 | 2497 | 2278 | 2077 | |
| | 10 mm | | | | |
| | bin1 | 1840 | 1602 | 1405 | |
| | bin2 | 2910 | 2612 | 2370 | |
| | bin3 | 2470 | 2252 | 2058 | |
| | : | : | | | |

FIG. 5C

PRESENT-MOMENT ALL-POINTS CORRECTIVE MATERIAL MAP (CORRECTIVE MEASUREMENT VALUES)

FIG. 6A

411 — CURRENT CORRECTIVE MATERIAL MAP (FIG. 5A)

| | | ACRYLIC | | | |
|---|---|---|---|---|---|
| | ENERGY | 0 mm | 50 mm | 100 mm | ... |
| ALUMINUM | 0 mm | bin1 | 2000 | 1748 | 1529 | |
| | | bin2 | 3000 | 2706 | 2441 | |
| | | bin3 | 2500 | 2280 | 2080 | |
| | 5 mm | bin1 | 1916 | 1675 | 1465 | |
| | | bin2 | 2954 | 2665 | 2404 | |
| | | bin3 | 2478 | 2261 | 2062 | |
| | 10 mm | bin1 | 1835 | 1605 | 1403 | |
| | | bin2 | 2909 | 2624 | 2367 | |
| | | bin3 | 2457 | 2241 | 2045 | |
| | : | : | | | | |

FIG. 6B 412-1 — PRESENT-MOMENT ALL-POINTS CORRECTIVE MATERIAL MAP (FIG. 5C)

| | | ACRYLIC | | | |
|---|---|---|---|---|---|
| | ENERGY | 0 mm | 50 mm | 100 mm | ... |
| ALUMINUM | 0 mm | bin1 | 2050 | 1784 | 1553 | |
| | | bin2 | 3100 | 2783 | 2499 | |
| | | bin3 | 2525 | 2302 | 2100 | |
| | 50 mm | bin1 | 1943 | 1690 | 1472 | |
| | | bin2 | 3004 | 2697 | 2421 | |
| | | bin3 | 2497 | 2278 | 2077 | |
| | 100 mm | bin1 | 1840 | 1602 | 1405 | |
| | | bin2 | 2910 | 2612 | 2370 | |
| | | bin3 | 2470 | 2252 | 2058 | |
| | : | : | | | | |

410 — MATERIAL DECOMPOSITION MAP

| | | FAT | | | |
|---|---|---|---|---|---|
| | ENERGY | 0 mm | 50 mm | 100 mm | ... |
| BONE | 0 mm | bin1 | 2000 | 1748 | 1529 | |
| | | bin2 | 3000 | 2706 | 2441 | |
| | | bin3 | 2500 | 2280 | 2080 | |
| | 2 mm | bin1 | 1916 | 1675 | 1465 | |
| | | bin2 | 2954 | 2665 | 2404 | |
| | | bin3 | 2478 | 2261 | 2062 | |
| | 4 mm | bin1 | 1835 | 1605 | 1403 | |
| | | bin2 | 2909 | 2624 | 2367 | |
| | | bin3 | 2457 | 2241 | 2045 | |
| | : | : | | | | |

FIG. 6D 410-1 — CORRECTED MATERIAL DECOMPOSITION MAP

| | | FAT | | | |
|---|---|---|---|---|---|
| | ENERGY | 0 mm | 50 mm | 100 mm | ... |
| BONE | 0 mm | bin1 | 2050 | 1825 | 1529 | |
| | | bin2 | 3100 | 3007 | 2441 | |
| | | bin3 | 2525 | 2478 | 2080 | |
| | 2 mm | bin1 | 1943 | 1809 | 1472 | |
| | | bin2 | 3004 | 2878 | 2421 | |
| | | bin3 | 2497 | 2442 | 2077 | |
| | 4 mm | bin1 | 1840 | 1733 | 1405 | |
| | | bin2 | 2910 | 2834 | 2370 | |
| | | bin3 | 2470 | 2420 | 2058 | |
| | : | : | | | | |

PHOTON COUNTING CT APPARATUS AND METHOD OF CORRECTING MATERIAL DECOMPOSITION MAP

BACKGROUND OF THE INVENTION

Field of the Invention

The present invention relates to an X-ray computed tomography (CT) apparatus having a photon counting mode (hereinafter referred to as a "PCCT apparatus"), and, more particularly relates to a technique to reduce statistical noise occurring at a low energy side in the PCCT apparatus.

Description of the Related Art

The X-ray CT apparatus is an apparatus which, while rotating, around a subject, a pair including an X-ray tube and an X-ray detector arranged opposite each other across the subject with a positional relationship between the pair retained, obtains X-ray transmissive data about the subject and reconstructs a tomographic image thereof (hereinafter referred to as a "CT image") by calculation, and is used as, for example, an inspection apparatus for industrial use or for security use or a diagnostic imaging apparatus for medical use.

With regard to an X-ray CT apparatus for medical use, a PCCT apparatus equipped with a photon counting mode is in the process of research and development. The PCCT apparatus uses a detector of the photon counting type to count quanta of X-rays (X-ray photons) transmitted through a subject with every detection element. This enables, for example, obtaining a spectrum available for estimating elements configuring an internal tissue of the subject through which X-rays have been transmitted, and thus obtaining an X-ray CT image subjected to material decomposition of the tissue of the subject (see Patent literature 1).

Moreover, the PCCT apparatus is able to discriminate the counted individual X-ray photons by energy values, thus obtaining X-ray intensities in respective energy bands (energy bins). With the use of this, the PCCT apparatus may be used to extract only X-rays in a specific energy range, convert the extracted X-rays into an image, and utilize the image for diagnosis.

On the other hand, Patent Literature 2 discloses a configuration which, to improve the accuracy of material decomposition in a PCCT apparatus, computationally calculates detection data caused by a non-linear response of a detector that detects photons. Then, such a disclosed configuration subtracts the calculated non-linear response data from data actually detected by the detector and performs material decomposition with use of detection data obtained by such subtraction.

LIST OF RELATED ART

Patent Literature

Patent Literature 1: JP-A-2019-176988
Patent Literature 2: JP-A-2016-193174

The PCCT apparatus performs correction processing on data obtained in each energy band counted by an X-ray detection element. For example, the PCCT apparatus performs linearity correction of a reference correction circuit, correction of logarithmic conversion processing, correction of offset processing, sensitivity correction, beam hardening correction, water phantom calibration, and CT value correction. Correction data for use in such correction is calculated based on data (Air data) which is obtained by radiating X-rays to the air without a subject being arranged and performing counting in every energy band with detection elements. Usually, Air data is obtained to determine correction data before the shipment of a PCCT apparatus or at the time of maintenance thereof.

However, a deviation may occur in the above-mentioned Air data between at the time of correction data calculation and at the time of actual image capturing of a subject, and there is an issue in which, if correction data calculated based on Air data with a deviation occurring therein is used to correct count data obtained at the time of image capturing of a subject, the accuracy of material decomposition decreases. The inventors of the present invention became aware that the cause of a deviation occurring in Air data depending on image capturing dates was the spectrum of X-rays generated by an X-ray tube varying by, for example, heat generated by the X-ray tube or by secular change thereof.

While the configuration disclosed in Patent Literature 2 obtains non-linear response data by computation and subtracts the obtained data from detection data, since a variation of the spectrum of X-rays caused by, for example, heat is also influenced by, for example, the ambient temperature of a place of installation of the PCCT apparatus or a time elapsed from powering-on thereof, it is not easy to accurately calculate detection data by computation.

SUMMARY OF THE INVENTION

Aspects of the present invention are directed to accurately performing material decomposition even if a variation in X-ray spectrum occurs in a PCCT apparatus.

According to an aspect of the present invention, a photon counting CT apparatus configured as described below is provided. The photon counting CT apparatus includes an X-ray tube that radiates X-rays to an imaging range, an X-ray detector that counts a plurality of X-ray photons passing through the imaging range in each of a plurality of energy bands according to energy levels of the respective X-ray photons, a map storage unit that stores a material decomposition map indicating measurement values in a plurality of energy bands previously obtained about combinations of two or more types of materials made to have a plurality of respective different thicknesses, a material decomposition unit that obtains, by referring to the material decomposition map, a combination of thicknesses of two or more types of materials corresponding to measurement values obtained by the X-ray detector performing counting about a plurality of energy bands in a state in which a subject is arranged in the imaging range, and a map correction unit that corrects the material decomposition map. The map correction unit actually measures corrective measurement values by radiating X-rays from the X-ray tube and counting X-ray photons in each of a plurality of energy bands in a state in which no subject is arranged in the imaging range and/or in a state in which one or more types of corrective materials are arranged at a position through which X-rays radiated from the X-ray tube pass, and corrects the measurement values in the material decomposition map based on the corrective measurement values.

According to an embodiment of the present invention, even if a variation in X-ray spectrum occurs in a PCCT apparatus, the map correction unit acquires corrective measurement values and corrects measurement values in the material decomposition map based on the corrective measurement values, so that it is possible to accurately perform material decomposition.

BRIEF DESCRIPTION OF THE DRAWINGS

FIG. 2 is a diagram used to explain that measurement values are measured with respect to a plurality of energy bands for each detection element (channel) in the photon counting CT apparatus according to the first embodiment.

FIG. 3 is a diagram illustrating an example of a material decomposition map (bed) in the photon counting CT apparatus according to the first embodiment.

FIGS. 5A, 5B, and 5C are explanatory diagrams illustrating a current corrective material map, a present-moment corrective material map, and a present-moment all-points corrective material map, respectively, in the photon counting CT apparatus according to the first embodiment.

FIGS. 6A, 6B, 6C, and 6D are explanatory diagrams illustrating a current corrective material map, a present-moment corrective material map, a material decomposition map, and a corrected material decomposition map, respectively, in the photon counting CT apparatus according to the first embodiment.

DESCRIPTION OF THE EMBODIMENTS

Figure 1:
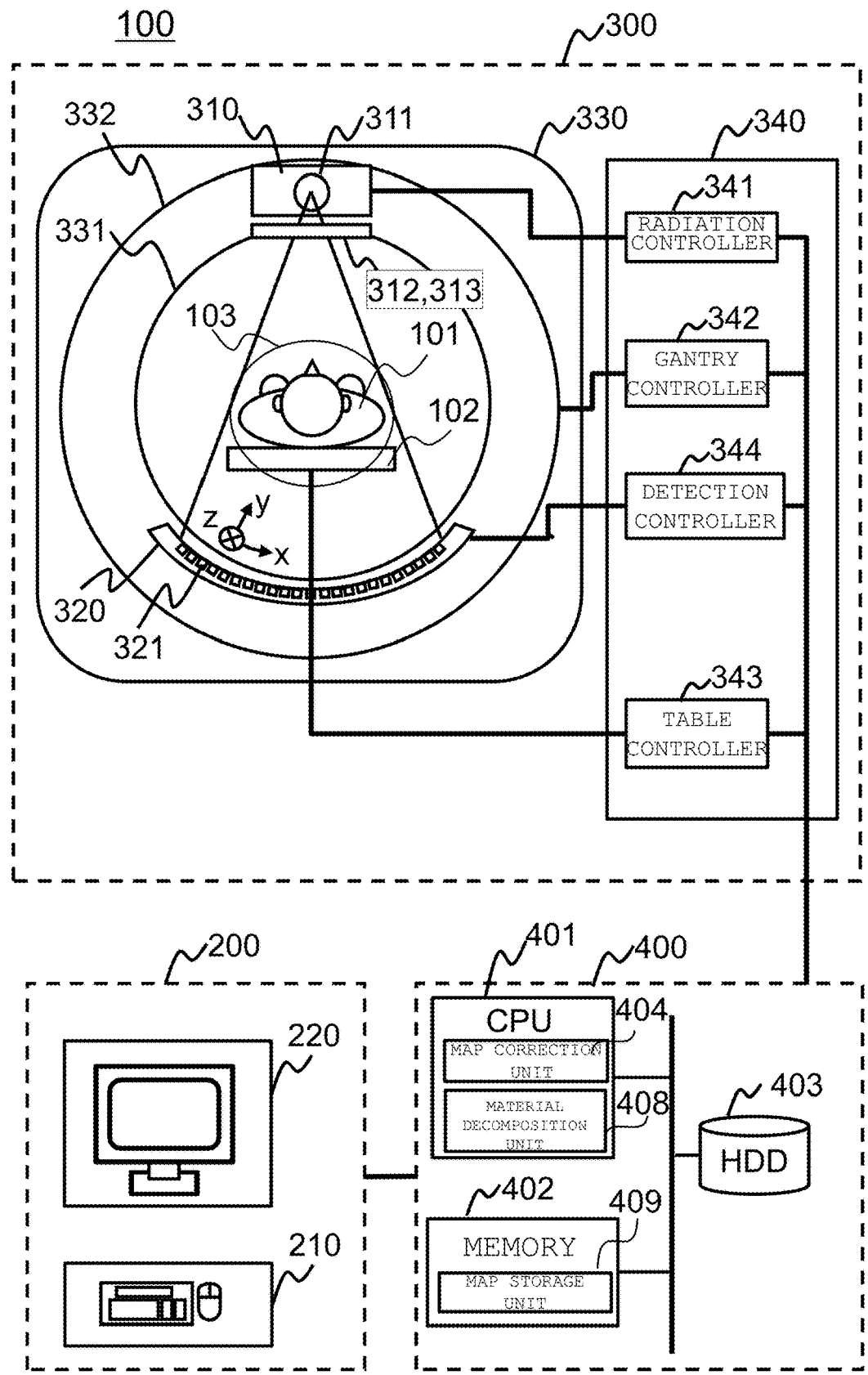
FIG. 1 is a block diagram illustrating a configuration of a photon counting CT apparatus according to a first embodiment of the present invention.

Examples of a photon counting CT apparatus according to embodiments of the present invention are described below. In the following description, in all of the figures used to describe embodiments of the present invention, elements or components having the respective same functions are assigned the respective same reference numerals and any repetitive descriptions thereof are omitted.

First Embodiment

An outline of a PCCT apparatus according to a first embodiment is described below with reference to FIG. 1.

The present embodiment is configured to actually measure measurement values obtained with X-rays at the time of image capturing of a subject 101 under a predetermined condition and correct a map (here, a bed) 410 for use in material decomposition with use of the actually measured measurement values. This enables accurately performing material decomposition even if a variation occurs in the spectrum of X-rays due to an X-ray tube 311 or a component arranged therearound being influenced by, for example, an increase in temperature of the X-ray tube 311.

A PCCT apparatus according to the present embodiment includes, as illustrated in FIG. 1 as an overall configuration thereof, the X-ray tube 311, which radiates X-rays to an imaging range 103, an X-ray detector 321, a rotary unit (rotary plate) 332, a map storage unit 409, a material decomposition unit 408, and a map correction unit 404.

The X-ray tube 311 has a configuration in which a cathode and an anode are arranged within a vacuum tube. Thermal electrons generated from the cathode collide with the anode rotating, so that X-rays are generated.

The X-ray detector 321 includes a plurality of detection elements (channels Ch 1 to Ch n) arrayed and a counting circuit and counts a plurality of X-ray photons passing through the imaging range 103 in each of a plurality of energy bands (bin 1 to bin k) according to energy levels of the respective X-ray photons as illustrated in FIG. 2.

The rotary unit 332 rotates the X-ray tube 311 and the X-ray detector 321 around the imaging range 103.

The map storage unit 409 stores a material decomposition map 410, which is used for material decomposition processing. The material decomposition map 410 is a map indicating measurement values previously obtained by the X-ray detector 321 performing actual measurement or calculation in a plurality of energy bands (bin 1 to bin k) in a case where a plurality of types of respective thicknesses (lengths through which X-rays pass) of two or more types of materials targeted for discrimination (here, a bone and a fat) is prepared and each of combinations thereof is arranged between the X-ray tube 311 and the X-ray detector 321, as illustrated in FIG. 3 as an example. While a bed is used as the material decomposition map 410 as illustrated in FIG. 3, the material decomposition map 410 can be expressed by, for example, a graph or mathematical expression.

The material decomposition unit 408 obtains, by referring to the material decomposition map 410, a combination of respective thicknesses (transmissive distances) of two or more types of materials which correspond to measurement values obtained by the X-ray detector 321 performing counting with regard to a plurality of energy bands in a state in which the subject 101 is arranged in the imaging range 103.

The map correction unit 404 radiates X-rays from the X-ray tube 311 in a vacant state in which the subject 101 is not arranged in the imaging range 103 (FIG. 4A) and/or in a state in which one or more types of corrective materials 104 are arranged between the X-ray tube 311 and the X-ray detector 321 (FIG. 4B) at desired timing such as timing before or after image capturing of the subject 101 or timing of powering-on of the PCCT apparatus, and performs counting in each of a plurality of energy bands, thus acquiring corrective measurement values 412 (FIG. 5B). The map correction unit 404 corrects measurement values in the material decomposition map 410 based on the acquired corrective measurement values 412.

The one or more types of corrective materials 104 as mentioned herein refer to one or more materials different in element or composition or one or more objects different in shape.

The elements or compositions of the corrective materials 104 can be the same materials as, or materials different from, materials in the material decomposition map 410 (for example, a bone and a fat). Furthermore, in a case where the elements or compositions of the corrective materials 104 are different from the materials in the material decomposition map 410, a relationship 61 between corrective measurement values 411 (FIG. 5A and FIG. 6A) obtained by performing counting in each of a plurality of energy bands with regard to the corrective materials 104 and measurement values (measurement values in the material decomposition map 410) (FIG. 3 and FIG. 6C) obtained by performing counting in each of a plurality of energy bands with regard to the materials in the material decomposition map 410 is previously measured with X-ray spectra. The map correction unit 404 uses the measured relationship 61 to correct measurement values in the material decomposition map 410 (FIG. 3 and FIG. 6C) based on corrective measurement values 412 or 412-1 (FIG. 5B or FIG. 6B), thus being able to create a corrected material decomposition map 410-1 (FIG. 6D).

For example, as illustrated in FIGS. 5A and 5B and FIGS. 6A and 6B, at least one of aluminum (Al) and acrylic plates can be used as the corrective material 104.

Moreover, in a case where the elements or compositions of the corrective materials 104 are different from materials in the material decomposition map 410, it is desirable that a current corrective material map 411 (FIG. 5A and FIG. 6A) created at the same time point as the time point of creation of the material decomposition map 410 be currently stored in the map storage unit 409. The current corrective material map 411 is a map indicating measurement values previously obtained by the X-ray detector 321 performing actual measurement or calculation with regard to a plurality of energy bands (bin 1 to bin k: in FIG. 5A and FIG. 6A, k=3) in a case where a plurality of types of respective different thicknesses of two or more types of corrective materials (Al and acrylic) 104 is prepared and each of combinations thereof is arranged between the X-ray tube 311 and the X-ray detector 321, as illustrated in FIG. 5A and FIG. 6A. The current corrective material map 411 is generated by a service engineer before the shipment of the PCCT apparatus or at the time of replacement of the X-ray tube 311 or the X-ray detector 321, and is then stored in the map storage unit 409.

It is desirable that the map correction unit 404 performs actual measurement of the corrective measurement values 412 (FIG. 5B) at the present moment, thus generating a map (hereinafter referred to as a "present-moment corrective material map 412"). As with the current corrective material map 411, the present-moment corrective material map 412 is a map indicating measurement values in each of a plurality of energy bands obtained with regard to each of combinations of a plurality of respective different thicknesses of two or more types of corrective materials (Al and acrylic) 104, and is generated by performing actual measurement of at least some measurement values at the present moment, so that X-ray spectra at the present moment can be reflected in the measurement values.

For example, corrective measurement values in each energy band are actually measured with regard to at least two combinations in the present-moment corrective material map 412 (two fields in the bed). Specifically, for example, corrective measurement values in each energy band actually measured in a vacant state in which the subject 101 is not arranged in the imaging range 103 (FIG. 4A) are used as corrective measurement values in fields in which both the thicknesses of two types of corrective materials (Al and acrylic) 104 in the map 412 illustrated in FIG. 5B are 0 centimeters (cm). Moreover, corrective measurement values in each energy band actually measured in a state in which only an acrylic plate with a thickness of 10 cm serving as a corrective material 104 is arranged in the imaging range 103 (FIG. 4B) are used as corrective measurement values in fields for a combination of an acrylic plate with a thickness of 10 cm and an Al plate with a thickness of 0 cm in the map 412 illustrated in FIG. 5B.

In this way, after obtaining corrective measurement values by actual measurement with regard to at least two portions (in FIG. 5B, three portions) of the present-moment corrective material map 412 illustrated in FIG. 5B, the map correction unit 404 calculates, by interpolation or extrapolation, measurement values for the remaining vacant fields in the present-moment corrective material map 412 illustrated in FIG. 5B while referring to the current corrective material map 411 illustrated in FIG. 5A.

An example of a calculation performed by the map correction unit 404 is described. A value for a field in the map illustrated in FIG. 5A is expressed by Ak_ac #x_al #y. "k" denotes a bin number (in FIG. 5A, 1 to 3), "x" of ac #x denotes the length (millimeter (mm)) of an acrylic plate in an X-ray transmission direction, and "y" of al #y denotes the length (mm) of an aluminum plate in an X-ray transmission direction. Moreover, a value for a field in the map illustrated in FIG. 5B is similarly expressed by Bk_ac #x_al #y. Additionally, a value for a field not yet subjected to measurement in the map illustrated in FIG. 5B is expressed by Ck_ac #x_al #y. For example, a value C for a position of "acrylic 50 mm" and "aluminum 0 mm" in FIG. 5B is obtainable by the following equation (1):

$$Ck\_ac\ \#50\_al\ \#0 = Ak\_ac\ \#50\_al\ \#0 \times (Bk\_ac\ \#100\_al\ \#0/Ak\_ac\ \#100\_al\ \#0 + Bk\_ac\ \#0\_al\ \#0/Ak\_ac\ \#0\_al\ \#0)/2 \quad (1)$$

In this way, the map correction unit 404 obtains, by interpolation, a position computable by interpolation from information about positions measured at the present moment or, if not so, calculates a ratio between "A" and "B" by extrapolation, and multiplies the original value of "A" by a result of such calculation, thus performing correction.

This enables generating a present-moment all-points corrective material map 412-1 (FIG. 5C). X-ray spectra at the present moment are reflected in the generated present-moment all-points corrective material map 412-1 illustrated in FIG. 5C.

Therefore, comparing the present-moment all-points corrective material map 412-1 (FIG. 6B) and the current corrective material map 411 (FIG. 6A) with each other as illustrated in FIGS. 6A and 6B enables recognizing a change in X-ray spectra occurring during that time as a change in measurement values. Correcting the measurement values in the material decomposition map 410 illustrated in FIG. 6C according to such a change in X-ray spectra enables obtaining a corrected material decomposition map 410-1 (FIG. 6D) associated with the change in X-ray spectra.

A method of correcting measurement values in the material decomposition map 410 to generate a corrected material decomposition map 410-1 is described with reference to FIGS. 6A to 6D.

First, the method obtains, by calculation, to which position (a ratio between acrylic and aluminum) in the current corrective material map 411 illustrated in FIG. 6A each position (for example, a fat 50 mm and a bone 2 mm) in the material decomposition map 410 illustrated in FIG. 6C corresponds. Since attenuation results of bins of respective signals obtained by transmission through a fat 50 mm and a bone 2 mm are previously obtained from the material decomposition map 410 illustrated in FIG. 6C, the calculation method obtains a ratio between the attenuation results and looks for a point in which an attenuation result coincident with the obtained ratio is obtainable in the current corrective material map 411 illustrated in FIG. 6A. However, while, since there is never a perfect coincidence, the obtained point includes an error, the calculation method obtains a point in which the error becomes minimum. The minimum error is defined as, for example, a place in which the sum of the squares obtained by squaring and summing differences of measurement values in the respective bins becomes minimum. The method obtains a correction value with regard to a position obtained as such on the current corrective material map 411 illustrated in FIG. 6A, by performing the following calculation:

Correction value=(Measurement value at an associated position in the present-moment all-points corrective material map 412-1 illustrated in FIG. 6B)/"Measurement value at the associated position in the current corrective material map 411 illustrated in FIG. 6A). The method multiplies the obtained correction value by a value at the associated position in the material decomposition map 410 illustrated in FIG. 6C. The method repeats this calculation, thus creating a corrected material decomposition map 410-1 (FIG. 6D) for a case where different materials are used.

The material decomposition unit 408 performs material decomposition on measurement values of a subject with use of the corrected material decomposition map 410-1.

Accordingly, in the PCCT apparatus according to the present embodiment, even if a change in X-ray spectra to be radiated occurs due to, for example, an increase in temperature of the X-ray tube 311, the map correction unit 404 acquires corrective measurement values and corrects the measurement values in the material decomposition map 410, so that the material decomposition unit 408 can accurately perform material decomposition.

Furthermore, to generate the present-moment corrective material map 412, the map correction unit 404 can radiate X-rays from the X-ray tube 311 in each of three states, i.e., a vacant state (Air) in which the subject 101 is not arranged in the imaging range 103, a state in which a first corrective material (for example, Al) with a predetermined thickness is arranged between the X-ray tube 311 and the X-ray detector 321, and a state in which a second corrective material (for example, acrylic) with a predetermined thickness is arranged between the X-ray tube 311 and the X-ray detector 321 and perform counting in each of a plurality of energy bands, thus actually measuring corrective measurement values. The map correction unit 404 corrects measurement values in the material decomposition map 410 with use of corrective measurement values actually measured in each of three states.

<Details of Configuration>

The PCCT apparatus 100 according to the present embodiment is described below in more detail. As illustrated in FIG. 1, the PCCT apparatus 100 according to the present embodiment includes a measuring unit 300, a computing unit 400, and a user interface (UI) unit 200.

The measuring unit 300 radiates X-rays to the subject 101 under the control of the computing unit 400 and measures X-ray photons transmitted through the subject 101. The measuring unit 300 includes, in addition to the X-ray tube 311 and an X-ray detection unit 320, a gantry 330, a control unit 340, and a bed 102, on which to place the subject 101. The control unit 340 includes a radiation controller 341, a gantry controller 342, a bed controller 343, and a detection controller 344.

An bore 331 is provided at the central portion of the gantry 330, and the subject 101 and the bed 102 are arranged within the bore 331. A rotary plate 332, on which the X-ray tube 311 and the X-ray detector 321 are mounted, and a drive mechanism (not illustrated), which is configured to rotate the rotary plate 332, are arranged inside the gantry 330. When the rotary plate 332 rotates a predetermined angle, the gantry controller 342 outputs a signal to the detection controller 344, the detection controller 344 outputs a signal to the X-ray detection unit 320, and the counting circuit of the X-ray detector 321 outputs counting data as data for one angle. Furthermore, for example, the diameter of the bore 331 of the gantry 330 is 700 mm. The distance between the X-ray generation point of the X-ray tube 311 and the X-ray entrance surface of the X-ray detector 321 is, for example, 1,000 mm.

The time required for one rotation of the rotary plate 332 is set by parameters input by the user via the UI unit 200. For example, if the required time is set as 1.0 seconds (s) per rotation, it is possible to set the number of times of image capturing per rotation to 900 times. Furthermore, in the present specification, the circumferential direction of the bore 331 is assumed to be an x-direction and the radial direction thereof is assumed to be a y-direction. A z-direction (the body axis direction of the subject 101) is a direction perpendicular to the x-direction and the y-direction.

An X-ray filter 312, which adjusts an X-ray spectrum, and a bowtie filter 313, which suppresses a dosage to a surrounding portion thereof, are arranged between the X-ray tube 311 and the imaging range 103, and thus configure an X-ray radiation unit 310. The X-ray tube 311 receives a high voltage supplied under the control of the radiation controller 341.

Figure 4A:
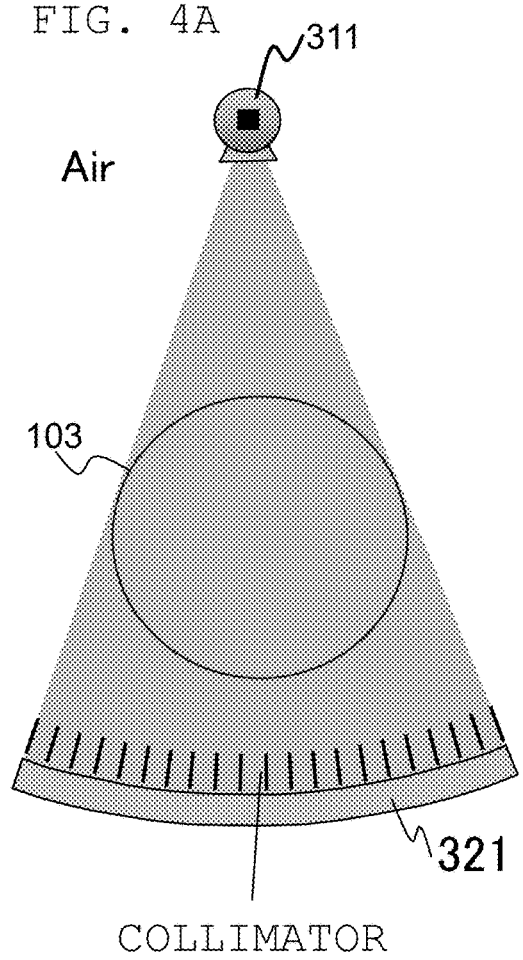
FIG. 4A is an explanatory diagram used to explain that, for the purpose of correction of a material decomposition map, with no subject arranged in an image capturing range, an X-ray detector actually measures X-ray photons.
Figure 4B:
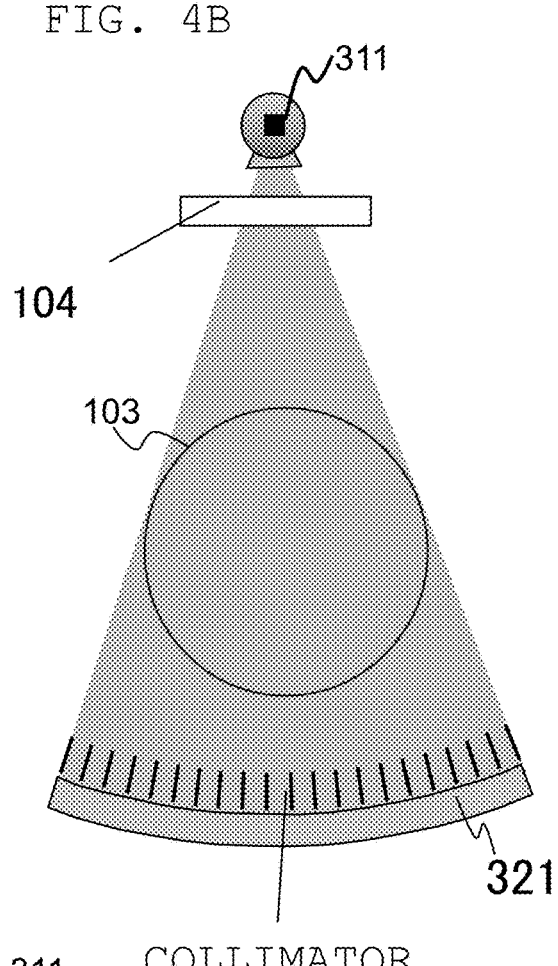
FIG. 4B is an explanatory diagram used to explain that, for the purpose of correction of a material decomposition map, with a corrective material arranged in the image capturing range, the X-ray detector actually measures X-ray photons.
Figure 4C:
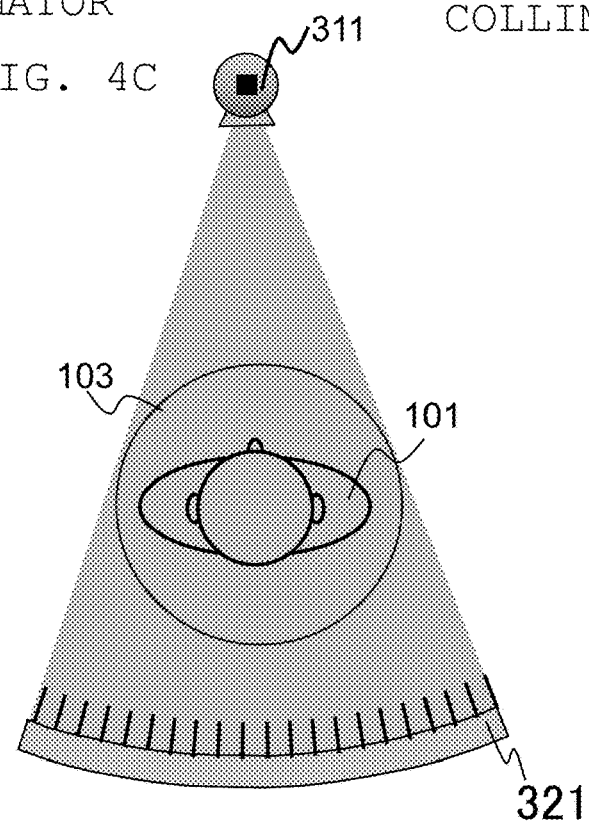
FIG. 4C is an explanatory diagram used to explain that image capturing of a subject is performed and material decomposition is performed with use of the corrected material decomposition map, each in the photon counting CT apparatus according to the first embodiment.

The X-ray detector 321 has a configuration in which a plurality of detection elements is arrayed. A plurality of X-ray detectors 321 is arranged in an arc form, so that the X-ray detection unit 320 is configured. As illustrated in FIGS. 4A to 4C, a collimator 323, which restricts incident directions of X-rays, is erected on the entrance surface side of the X-ray detector 321. The detection elements, which configure the X-ray detector 321, to be used includes semiconductor elements. Furthermore, the size in the x-direction of each detection element is, for example, 1 mm.

Figure 7:
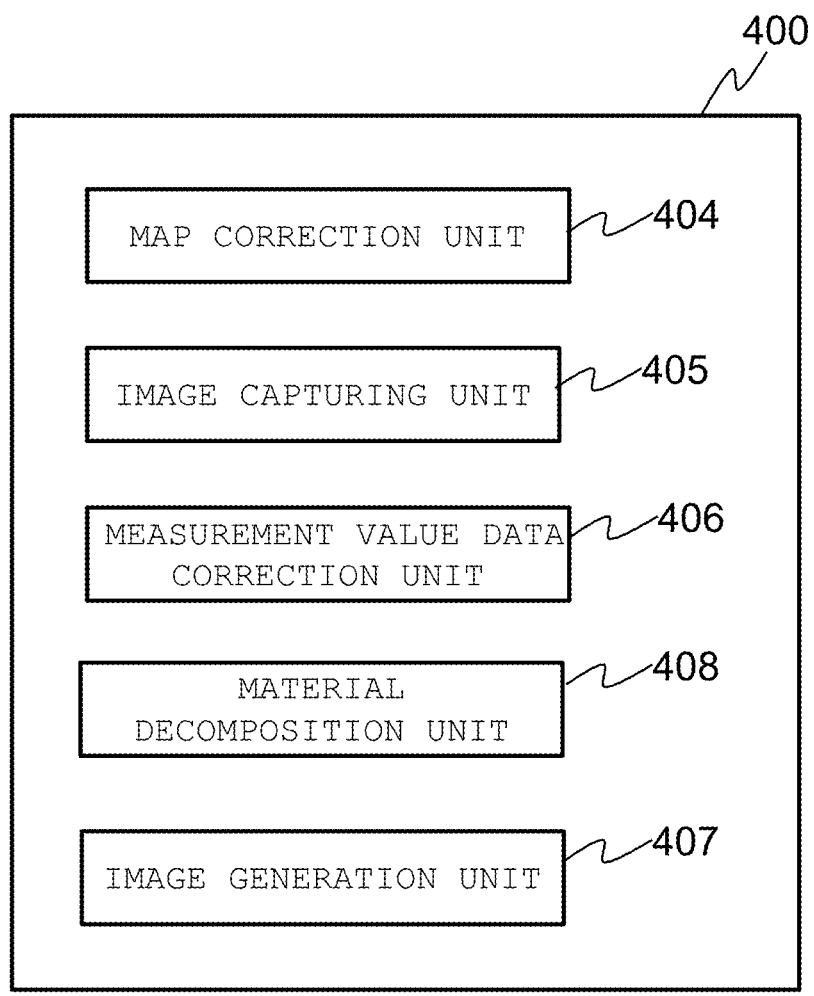
FIG. 7 is a functional block diagram of a computing unit of the photon counting CT apparatus according to the first embodiment.

The computing unit 400 controls the overall operation of the PCCT apparatus 100 and processes data acquired by the measuring unit 300, thus performing image capturing. The computing unit 400 includes a central processing unit (CPU) 401, a memory 402, and a hard disk drive (HDD) device 403. The computing unit 400 includes, as illustrated in the functional block diagram of FIG. 7, the functions of a map correction unit 404, an image capturing unit 405, a measurement value data correction unit 406, a material decomposition unit 408, and an image generation unit 407.

The CPU 401 loads a program previously stored in the HDD device 403 onto the memory 402 and executes the loaded program, thus implementing the above-mentioned functions by software. Furthermore, the whole or a part of the functions of the computing unit 400 can be implemented by, for example, an integrated circuit such as an application specific integrated circuit (ASIC) or a field-programmable gate array (FPGA).

The image capturing unit 405 performs image capturing such as CT imaging or scanogram. The measurement value data correction unit 406 performs correction processing on measurement value data collected in each energy band. The correction processing as mentioned herein includes, for example, linearity correction of a reference correction circuit, logarithmic conversion processing, offset processing, sensitivity correction, beam hardening correction, water phantom calibration, and CT value correction.

The material decomposition unit 408 performs conversion from measurement value data corrected by the measurement value data correction unit 406 into transmissive distances (for example, a bone 1 cm and a fat 5 cm) of materials configuring the subject 102.

The image generation unit 407 virtually reconstructs, with use of a conversion result obtained by the material decomposition unit 408, an image obtained by extracting only a bone, an image obtained by extracting only a fat, or a CT image obtained by radiating X-rays in a specific energy band.

The HDD device 403 stores, for example, data which is used for processing and data which is a result of processing.

The UI unit 200 includes an input device 210, such as a keyboard and a mouse, and an output device 220, such as a display device, and receives, from the user, for example, timing at which to correct the material decomposition map 410, the type of an image intended to be output, and an image capturing conditions and outputs such received information to the computing unit 400. The image capturing condition includes, for example, a tube current and tube voltage for the X-ray tube 311 and an image capturing range for the subject 101.

Next, image capturing processing which the computing unit 400 performs is described with reference to the flowchart of FIG. 8.

<Step S1101>

First, the map correction unit 404 determines whether the present moment is previously-determined timing at which to perform correction of the material decomposition map 410, and, if it is determined that the present moment is timing of map correction (Yes in step S1101), the map correction unit 404 advances the processing to step S1102. If it is determined that the present moment is not timing of map correction (No in step S1101), the map correction unit 404 advances the processing to step S1104.

Here, the previously-determined timing of map correction is timing set by the user, and includes, as setbed timing, for example, before image capturing, halfway through image capturing, after image capturing, and timing of powering-on in the morning.

<Step S1102>

When the present moment is timing at which to perform correction of the material decomposition map 410, the map correction unit 404 actually measures measurement values with regard to two types of corrective materials (Al and acrylic) 104 at the present moment and generates a corrective material map 412 based on the measured measurement values.

Step S1102 is specifically described as follows with reference to the flowchart of FIG. 9.

(Step S2001)

The map correction unit 404 radiates X-rays from the X-ray tube 311 as illustrated in FIG. 4A in a vacant state (Air) in which the subject 101 is not arranged in the imaging range 103, and actually measures corrective measurement values in each of a plurality of energy bands with the X-ray detector 321.

(Step S2002)

The map correction unit 404 causes the output device (display device) 220 to display an indication for prompting the user to arrange only an acrylic plate with a thickness of 10 cm, which is a corrective material 104, between the X-ray tube 311 and the imaging range 103, and, if the user has arranged the acrylic plate, the map correction unit 404 radiates X-rays from the X-ray tube 311 in that state (FIG. 4B) and actually measures corrective measurement values 412 in each of a plurality of energy bands with the X-ray detector 321.

(Step S2003)

The map correction unit 404 uses the measurement values obtained in steps S2001 and S2002 as corrective measurement values in fields for thicknesses of 0 cm of the corrective materials (Al and acrylic) 104 in the present-moment corrective material map 412 and fields for thicknesses of 10 cm in acrylic and 0 cm in Al therein, and calculates measurement values in remaining vacant fields by interpolation and extrapolation. This results in generation of the present-moment corrective material map 412 (FIG. 5B).

<Step S1103>

The map correction unit 404 compares the generated present-moment corrective material map 412 (FIG. 5B) and the current corrective material map 411 (FIG. 5A) with each other, and corrects measurement values in the material decomposition map 410 (FIG. 3 and FIG. 6C) according to a result of comparison.

<Steps S1104 and S1105>

If receiving an instruction for starting image capturing from the user via the UI unit 200 (Yes in step S1104), the image capturing unit 405 advances the processing to step S1105, in which the image capturing unit 405 radiates X-rays from the X-ray tube 311 to the subject 101 arranged in the imaging range 103 as illustrated in FIG. 4C and measures measurement values in a plurality of energy bands with the X-ray detector 321.

<Step S1106>

The material decomposition unit 408 obtains, by referring to the material decomposition map 410 corrected in step S1103, a combination of thicknesses (transmissive distances) of two or more types of materials corresponding to the measurement values about the subject 101 acquired in step S1105.

<Steps S1107 and S1108>

The image generation unit 407 generates, by computation, an image obtained by extracting a desired material (for example, only a bone or only a fat) or an X-ray CT image obtained in the case of radiating X-rays with a specific energy (for example, 60 electron volts (eV)) based on the transmissive distances of materials obtained by the material decomposition unit 408 in step S1106. The image generation unit 407 causes the output device 220 to display the generated image.

Even in a case where X-ray spectra have changed due to, for example, an increase in temperature of the X-ray tube 311, the present embodiment actually measures a change in measurement values at the present moment and corrects a material decomposition map, and is, therefore, able to improve the accuracy of material decomposition. Therefore, the doctor is enabled to make a diagnosis while viewing an image obtained by accurate material decomposition.

Second Embodiment

A PCCT apparatus according to a second embodiment is described.

The second embodiment uses, as a corrective material 104, a cylindrical phantom made of resin the attenuation of which becomes almost the same as that of the subject 101. For example, the second embodiment uses a cylindrical phantom made of polyethylene.

Figure 9:
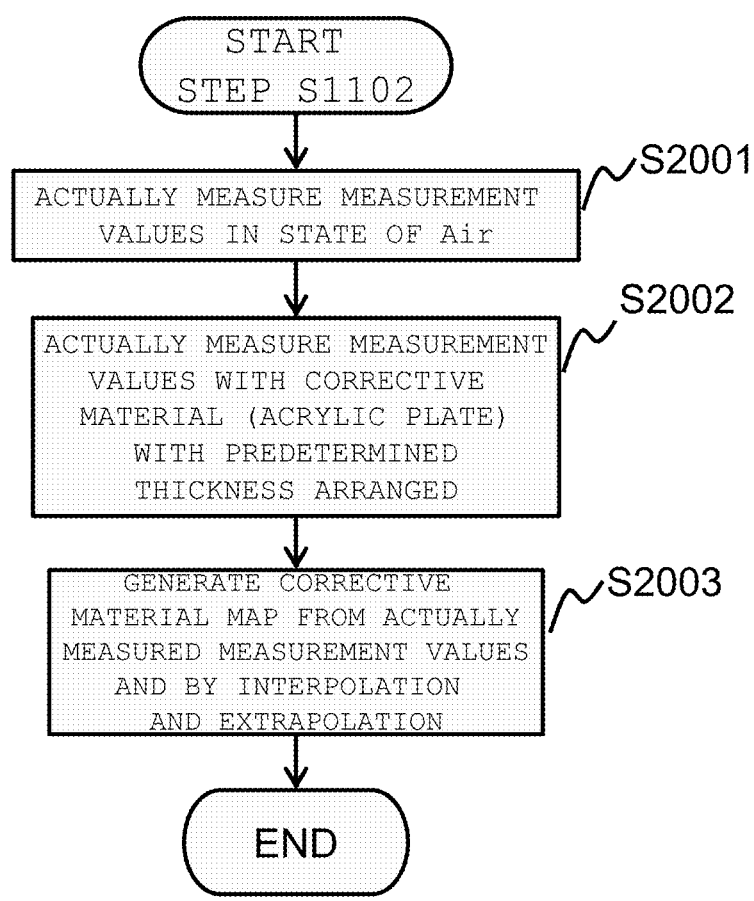
FIG. 9 is a flowchart illustrating the flow of image capturing processing according to the first embodiment.

In step S2001 in the flowchart of FIG. 9 in the first embodiment, the map correction unit 404 actually measures measurement values in a vacant state (Air) in which the subject 101 is not arranged in the imaging range 103, and then in step S2002, the map correction unit 404 actually measures measurement values with the cylindrical phantom arranged in the imaging range 103. In step S2003, the map correction unit 404 generates a present-moment corrective material map 412 which includes, as two elements thereof, measurement value data actually measured in a vacant state in which the subject 101 is not arranged and measurement value data actually measured with the cylindrical phantom made of resin arranged.

As the current corrective material map 411, a map which includes, as two elements thereof, measurement value data actually measured in a vacant state (Air) and measurement value data actually measured with the cylindrical phantom arranged is also current.

Figure 8:
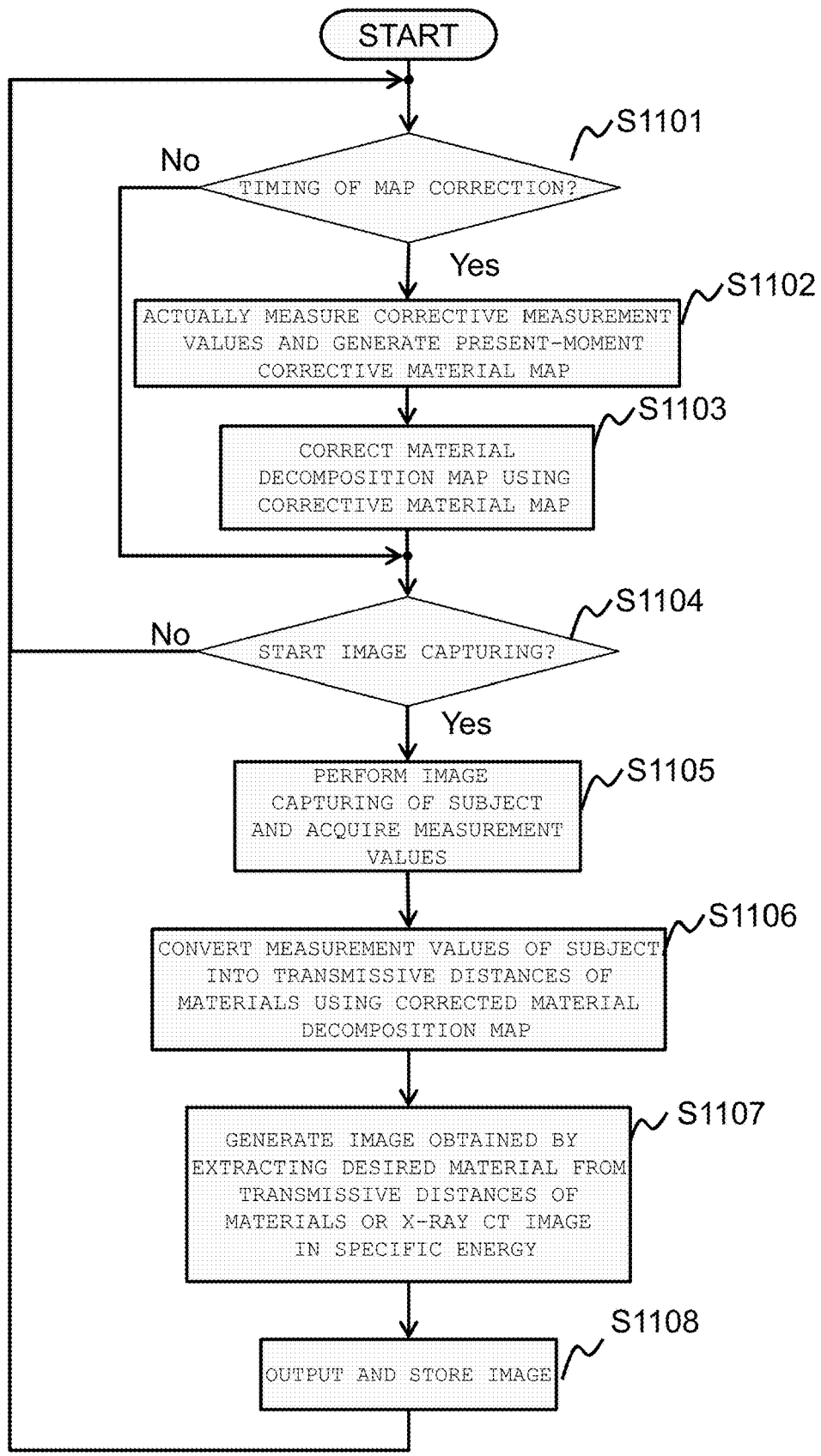
FIG. 8 is a flowchart illustrating the flow of image capturing processing according to the first embodiment.

In step S1102 illustrated in FIG. 8, the map correction unit 404 corrects the material decomposition map 410 based on a difference between the present-moment corrective material map 412 and the current corrective material map 411, thus obtaining the corrected material decomposition map 410-1.

The other configurations, processing operations, and advantageous effects are similar to those in the first embodiment.

Third Embodiment

A PCCT apparatus according to a third embodiment is described with reference to FIGS. 10A and 10B.

While each of the PCCT apparatuses according to the first and second embodiments is configured to actually measure corrective measurement values with the X-ray detector 321, the map correction unit 404 in the third embodiment further includes a reference detector 902 in addition to the X-ray detector 321 and actually measures corrective measurement values with the reference detector 902.

Figure 10:
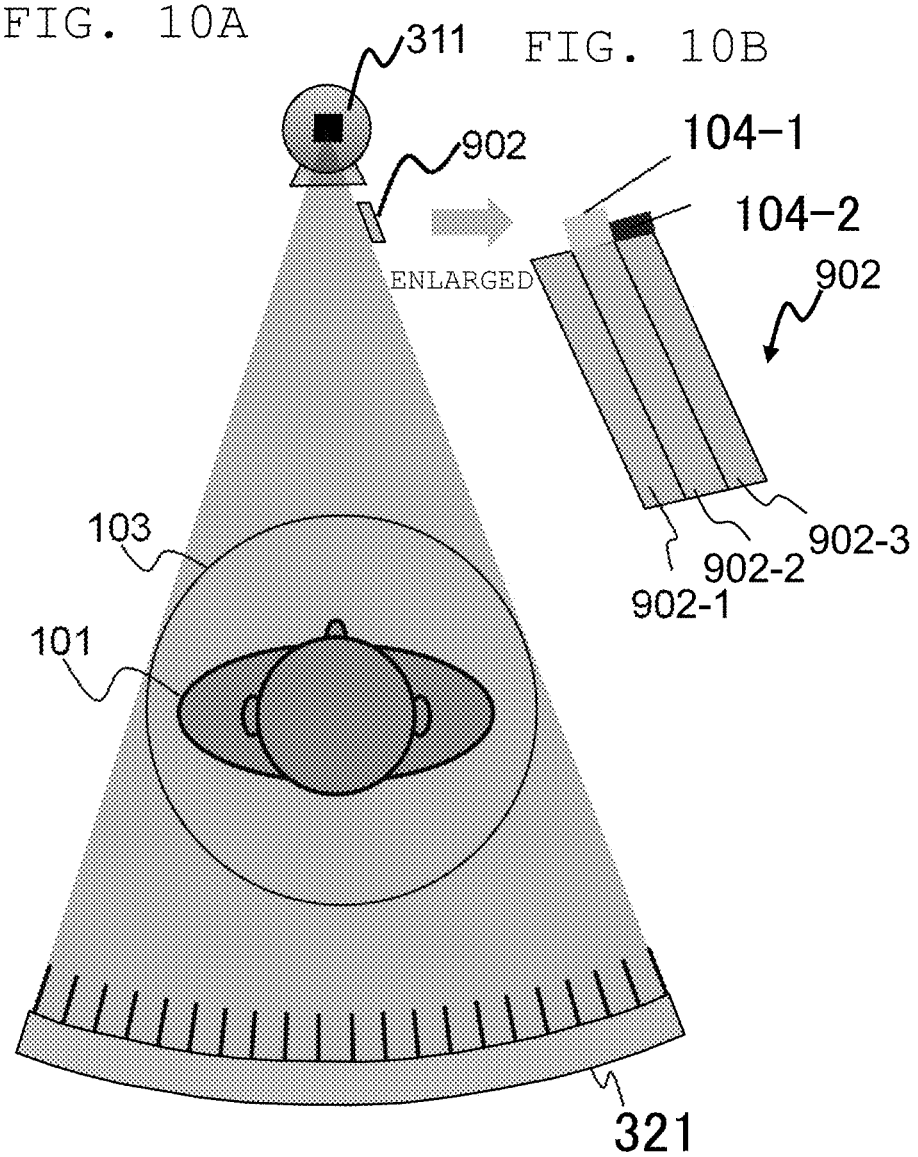
FIGS. 10A and 10B are explanatory diagrams illustrating a configuration of a part of a photon counting CT apparatus according to a third embodiment of the present invention.

The reference detector 902 is arranged at a position at which X-rays radiated from the X-ray tube 311 and passing outside the imaging range 103 arrive, as illustrated in FIG. 10A. Accordingly, actually measuring corrective measurement values with the reference detector 902 enables actually measuring corrective measurement values even during image capturing of a subject and thus correcting the material decomposition map 410 (FIG. 3 and FIG. 6C) in real time.

Moreover, since the reference detector 902 is present outside the imaging range 103, if none is arranged between the reference detector 902 and the X-ray tube 311, measurement values in the state of Air are obtained and, if a corrective material 104 with a predetermined thickness is arranged in front of the reference detector 902, measurement values about the arranged corrective material 104 are obtained. Therefore, if, as illustrated in FIG. 10B, a reference detector 902 including a plurality of detection elements 902-1 to 902-3 is used, none is arranged in front of the detection element 902-1, and corrective materials 104-1 and 104-2 different in thickness or material are previously arranged in front of the detection elements 902-2 and 902-3, respectively, it is possible to obtain corrective measurement values in the state of Air and about two types of corrective materials at one time. Therefore, it is possible to quickly generate the present-moment corrective material map 412.

Moreover, since the reference detector 902 is arranged outside the imaging range 103 and it is, therefore, possible to perform image capturing of the subject 101 with the reference detector 902 remaining arranged, there is also such an advantage that the user is not required to attach or detach the corrective material 104 at a position through which X-rays radiated from the X-ray tube 311 pass and the material decomposition map 410 is able to be automatically corrected.

Figure 11:
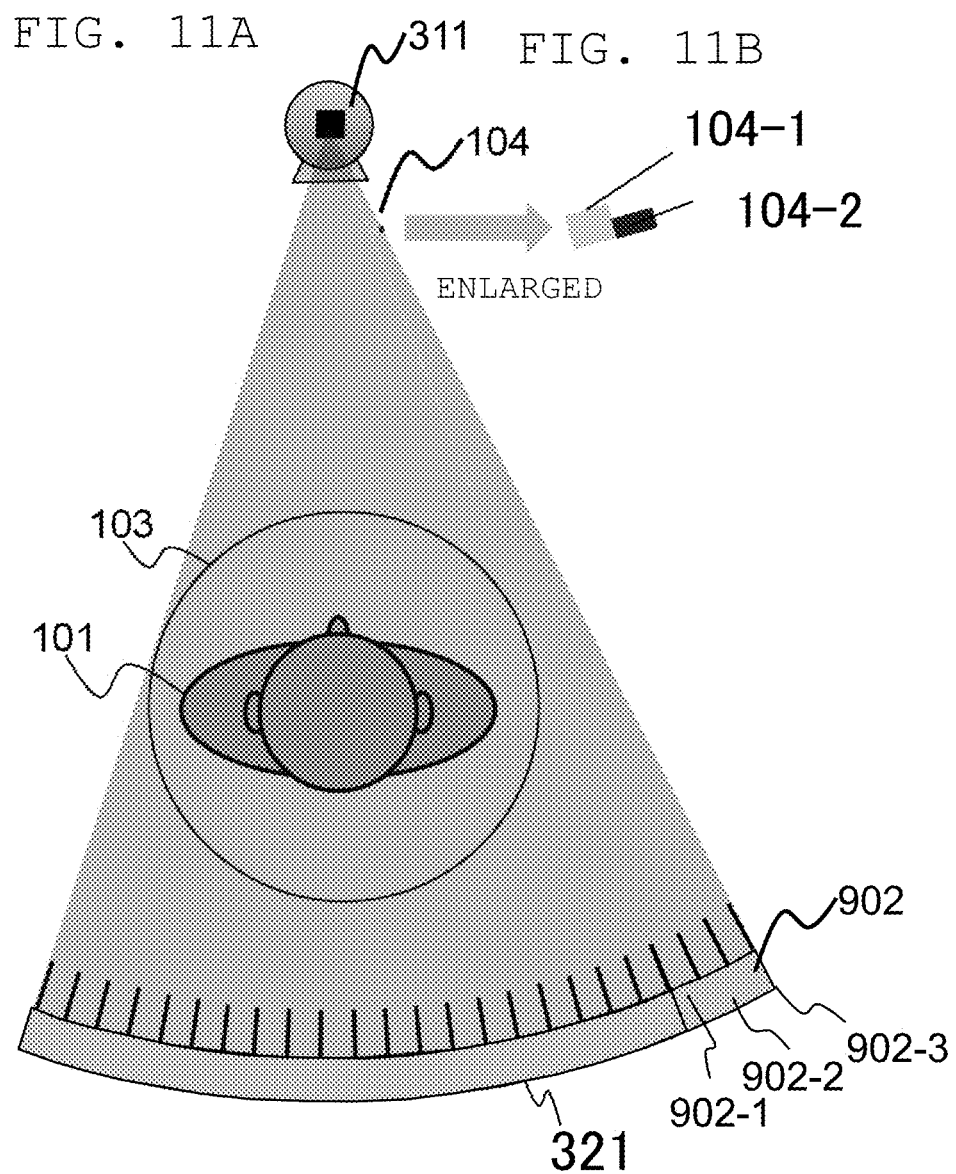
FIGS. 11A and 11B are explanatory diagrams illustrating another configuration of a part of the photon counting CT apparatus according to the third embodiment.

Additionally, the reference detector 902 is located outside the subject 101 and is, therefore, not influenced by the subject 101. Taking the advantage of this feature, it is possible to use, as the reference detector 902, an end portion of the X-ray detector 321, which detects X-rays transmitted through the subject 101, as illustrated in FIGS. 11A and 11B. In this case, there is such an advantage that the X-ray detector 321 and the reference detector 902 can be integrated.

Furthermore, in the present embodiment, it is desirable that the current corrective material map 411 be also generated with use of measurement values detected by the reference detector 902.

The other configurations are similar to those in the first embodiment and is, therefore, omitted from description.

Fourth Embodiment

Figure 12:
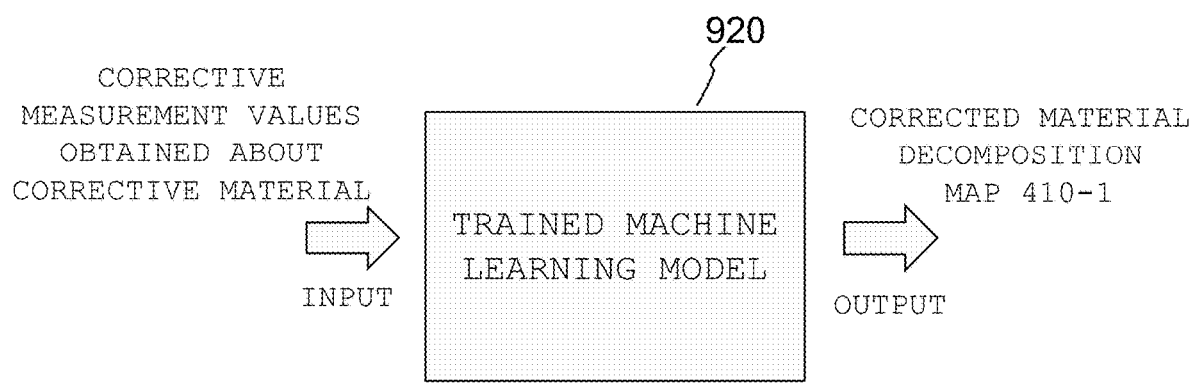
FIG. 12 is a block diagram illustrating a configuration of a part of a photon counting CT apparatus according to a fourth embodiment of the present invention.

A PCCT apparatus according to a fourth embodiment is described with reference to FIG. 12.

While the PCCT apparatus according to each of the first to third embodiments has a configuration in which, after actually measuring corrective measurement values, the map correction unit 404 generates the present-moment corrective material map 412 by computation and then corrects the material decomposition map 410, the map correction unit 404 in the fourth embodiment uses a trained learning model 920, inputs actually measured corrective measurement values to the learning model 920, and then directly obtains the corrected material decomposition map 410-1 as an output of the learning model 920. The learning model 920 to be used can be a known one and can be, for example, a neural network.

To train the learning model 920, the corrective measurement values obtained by the respective methods in the first to third embodiments can be used as input data and the corrected material decomposition map 410-1 can be used as correct answer data, so that the learning model 920 can be trained in advance sufficiently by machine learning or deep learning.

This enables the map correction unit 404 to obtain the corrected material decomposition map 410-1 by only actually measuring corrective measurement values and inputting the measured corrective measurement values to the learning model 920, so that it is possible to accurately perform correction of the material decomposition map 410 in a short amount of time.

A corrective measurement value which the map correction unit 404 inputs to the learning model 920 only needs to be 1 or more, and can be, for example, only measurement values in a plurality of energy bands actually measured in a vacant state (Air) in which no subject is arranged in the imaging range 103, and, additionally, measurement values actually measured with one or more types of corrective materials 104 arranged can be input to the learning model 920.

Furthermore, data to be output from the trained learning model can be set to be not the material decomposition map 410 but the present-moment corrective material map 412. In this case, the map correction unit 404 can correct the material decomposition map 410 by performing processing similar to that in the first embodiment with use of the obtained corrective measurement values 412, thus obtaining the corrected material decomposition map 410-1.

In the fourth embodiment, the configurations, processing operations, and advantageous effects other than processing in which the map correction unit 404 obtains the corrected material decomposition map 410-1 are similar to those in the first to third embodiments and, therefore, the detailed description thereof is omitted.

DESCRIPTION OF REFERENCE NUMERALS

100: PCCT apparatus, 101: subject, 102: bed, 200: UI unit, 210: input device, 220: output device, 300: measuring unit, 310: X-ray radiation unit, 311: X-ray tube, 312: X-ray filter, 313: bowtie filter, 320: X-ray detection unit, 321: X-ray detector, 322: detection element, 330: gantry, 331: bore, 332: rotary plate, 340: control unit, 341: radiation controller, 342: gantry controller, 343: bed controller, 344: detection controller, 400: computing unit, 401: central processing unit, 402: memory, 403: HDD device, 404: map correction unit, 405: image capturing unit, 406: measurement value data correction unit, 407: image generation unit, 408: material decomposition unit, 409: map storage unit, 410: material decomposition map.

What is claimed is:

1. A photon counting computed tomography (CT) apparatus comprising:
an X-ray tube that radiates X-rays to an imaging range;
an X-ray detector that counts a plurality of X-ray photons passing through the imaging range in each of a plurality of energy bands according to energy levels of the respective X-ray photons;
a map storage unit that stores a material decomposition map indicating measurement values in a plurality of energy bands previously obtained about combinations of two or more types of materials made to have a plurality of respective different thicknesses;
a material decomposition unit that obtains, by referring to the material decomposition map, a combination of thicknesses of two or more types of materials corresponding to measurement values obtained by the X-ray detector performing counting about a plurality of energy bands in a state in which a subject is arranged in the imaging range; and
a map correction unit that corrects the material decomposition map,
wherein the map correction unit actually measures corrective measurement values by radiating X-rays from the X-ray tube and counting X-ray photons in each of a plurality of energy bands in a state in which no subject is arranged in the imaging range and/or in a state in which one or more types of corrective materials are arranged at a position through which X-rays radiated from the X-ray tube pass, and corrects the measurement values in the material decomposition map based on the corrective measurement values.

2. The photon counting CT apparatus according to claim 1, wherein the map correction unit actually measures the corrective measurement values at timing before image capturing of the subject or after image capturing thereof with the X-ray detector.

3. The photon counting CT apparatus according to claim 1, wherein the map correction unit includes a reference detector that detects X-ray photons, located at a position at which X-rays radiated from the X-ray tube and passing outside the imaging range arrive, and actually measures the corrective measurement values at any one of timing before image capturing of the subject, timing during image capturing thereof, and timing after image capturing thereof.

4. The photon counting CT apparatus according to claim 1, wherein the one or more types of corrective materials are one or more types of materials different in element or composition or one or more types of materials different in shape.

5. The photon counting CT apparatus according to claim 1, wherein the corrective material and a material in the material decomposition map are different from each other, and
wherein the map correction unit uses a previously obtained relationship between corrective measurement values counted in each of the plurality of energy bands about the corrective material and measurement values counted in each of the plurality of energy bands about the two or more types of materials in the material decomposition map to correct the measurement values in the material decomposition map based on the corrective measurement values.

6. The photon counting CT apparatus according to claim 1, wherein the map correction unit actually measures corrective measurement values by radiating X-rays from the X-ray tube and performing counting in each of the plurality of energy bands in each of three conditions including a vacant state in which no subject is arranged in the imaging range, a state in which a first corrective material with a predetermined thickness is arranged between the X-ray tube and the X-ray detector, and a state in which a second corrective material with a predetermined thickness is arranged between the X-ray tube and the X-ray detector, and corrects the measurement values in the material decomposition map with use of the corrective measurement values actually measured in each of the three conditions.

7. The photon counting CT apparatus according to claim 1, wherein the material decomposition map is generated with use of measurement values obtained by radiating X-rays from the X-ray tube and performing counting in each of the plurality of energy bands in a vacant state in which no subject is arranged in the imaging range and measurement values obtained by radiating X-rays from the X-ray tube and performing counting in each of the plurality of energy bands in a state in which a combination of the two or more types of materials made to have a plurality of respective different thicknesses is arranged between the X-ray tube and the X-ray detector.

8. The photon counting CT apparatus according to claim 1, wherein thicknesses of the two or more types of materials in the material decomposition map include a thickness of zero.

9. The photon counting CT apparatus according to claim 1, wherein the map correction unit uses measurement value data actually measured in each of a vacant state in which no subject is arranged in the imaging range and a state in which one or more types of corrective materials are arranged at a position through which X-rays pass, as measurement value data in a map about combinations of two or more types of corrective materials made to have respective different thicknesses, and obtains measurement value data by interpolation and/or extrapolation with regard to combinations of thicknesses about which there is no measurement value data, thus generating the map.

10. The photon counting CT apparatus according to claim 1, wherein the map correction unit uses a cylindrical phantom made of resin as the one or more types of corrective materials.

11. The photon counting CT apparatus according to claim 1, wherein the map correction unit includes a trained learning model, inputs the corrective measurement values as input data to the learning model, and acquires the corrected material decomposition map as output data.

12. A method of correcting a material decomposition map for a photon counting computed tomography (CT) apparatus, the method comprising:
    actually measuring corrective measurement values by radiating X-rays from an X-ray tube and counting X-ray photons in each of a plurality of energy bands in a vacant state in which no subject is arranged in an imaging range of the photon counting CT apparatus and/or in a state in which one or more types of corrective materials are arranged at a position through which X-rays radiated from the X-ray tube pass; and
    correcting measurement values in a material decomposition map based on the actually measured corrective measurement values.

* * * * *